United States Patent [19]

Beck et al.

[11] Patent Number: 4,808,572
[45] Date of Patent: Feb. 28, 1989

[54] α-HYDROXY THIOETHERS

[75] Inventors: Andreas Beck, Freiburg, Fed. Rep. of Germany; Werner Breitenstein, Basel, Switzerland; Andreas von Sprecher, Oberwil, Switzerland; Robert W. Lang, Pratteln, Switzerland; Konrad Oertle, Therwil, Switzerland

[73] Assignee: Ciba-Geigy Corporation, Ardsley, N.Y.

[21] Appl. No.: 936,671

[22] Filed: Dec. 1, 1986

[30] Foreign Application Priority Data

Dec. 6, 1985 [CH] Switzerland ............. 5228/85

[51] Int. Cl.$^4$ ............. C07C 149/243; A61K 31/22
[52] U.S. Cl. ............. 514/18; 530/331; 560/15; 560/16; 560/106; 560/110; 560/152; 560/153; 560/250; 560/251; 560/252; 560/253; 560/262; 560/264; 560/266; 562/426; 562/556; 562/557; 562/581; 564/153; 564/154; 564/162; 564/198; 564/203; 514/532; 514/533; 514/534; 514/542; 514/544; 514/547; 514/549; 514/550; 514/562; 514/571; 514/557; 514/616; 514/618; 514/626; 514/625; 514/627; 514/628
[58] Field of Search ............. 560/16, 15, 152, 153, 560/106, 110, 250, 251, 252, 253, 262, 264, 266; 562/426, 556, 557, 581; 564/153, 154, 162, 198, 203; 530/331; 514/18, 532, 533, 534, 542, 544, 547, 549, 550, 562, 571, 557, 616, 618, 626, 625, 627, 628

[56] References Cited

U.S. PATENT DOCUMENTS

| | | | |
|---|---|---|---|
| 4,461,775 | 7/1984 | Stanley | 562/581 |
| 4,513,005 | 4/1985 | Baker | 562/426 |
| 4,533,747 | 8/1985 | Gleason | 562/581 |
| 4,552,893 | 11/1985 | Gleason | 562/581 |
| 4,649,215 | 3/1987 | Sprecher | 562/581 |

FOREIGN PATENT DOCUMENTS 0123543 10/1984 European Pat. Off. .

Primary Examiner—Michael L. Shippen
Attorney, Agent, or Firm—Irving M. Fishman

[57] ABSTRACT

Novel asymmetric thioethers of the formula

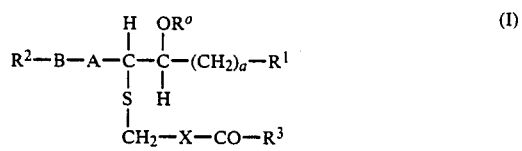

in which the general symbols have the following meanings:

a is an integer of from 1 to 7,
$R^o$ represents hydrogen or $C_{1-7}$-alkanoyl,
$R^1$ represents $C_{1-3}$-alkyl which may be substituted at the terminal carbon atom by a free or acylated hydroxy group, by a halogen atom having an atomic number of at most 17, or by methoxy, or represents $C_{1-3}$-perfluoroalkyl,
$R^2$ represents an optionally unsaturated aliphatic radical having from 5 to 15 carbon atoms,
A represents ethylene or alternatively, if $R^1$ represents a halogenated radical and/or B represents phenylene or ethylene, a single bond or vinylene,
B represents a single bond, ethynylene or phenylene,
$R^3$ represents hydroxy, $C_{1-7}$-alkoxy or an optionally substituted amino group, and
—X— represents a single bond, a methylene group of an optionally N-acylated primary aminomethylene group, and their salts are active as leucotriene antagonists since they eliminate the contractions of smooth muscles brought about by leucotrienes, and are therefore suitable for the treatment of allergic, especially asthmatic, conditions.

29 Claims, No Drawings

α-HYDROXY THIOETHERS

The invention relates to novel asymmetric α-hydroxy thioethers derived from the residue (M) of a mercaptoalkanecarboxylic acid, such as mercaptoacetic acid or β-mercaptopropionic acid, of a cysteine or cysteine peptide optionally acylated at the nitrogen atom, or of a salt or of a derivative, modified at the carboxy group, of such an acid, the sulphur atom of which is substituted by a linear radical (L) having at least 11 carbon atoms, which radical carries on one side of its chain, in the α-position to the sulphur atom, a hydroxy group that is preferably trans-orientated in relation to the S-atom, and on the other side may have one or more double bonds and/or a phenylene ring.

The invention relates especially to compounds of the formula

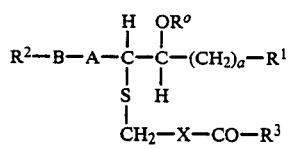

in which the general symbols have the following meanings:

a is an integer of from 1 to 7, $R^o$ represents hydrogen or $C_{1-7}$-alkanoyl, $R^1$ represents $C_{1-3}$-alkyl which may be substituted at the terminal carbon atom by a free or acylated hydroxy group, by a halogen atom having an atomic number of at most 17, or by methoxy, or represents $C_{1-3}$-perfluoroalkyl, $R^2$ represents an optionally unsaturated aliphatic radical having from 5 to 15 carbon atoms, A represents ethylene or alternatively, if $R^1$ represents a halogenated radical and/or B represents phenylene or ethylene, a single bond or vinylene, B represents a single bond, ethynylene or phenylene, $R^3$ represents hydroxy, $C_{1-7}$-alkoxy or an optionally substituted amino group, and —X— represents a single bond, a methylene group or an optionally N-acylated primary aminomethylene group, and to salts of such compounds having salt-forming properties.

The spatial representation in the above formula I for the preferred compounds, in which the O-atom of the hydroxy group is in the trans-configuration relative to the S-atom, is to be understood as follows: the symbols of the first line lie above, and those of the third line therefore below, the plane of representation (or vice-versa), which for the formula shown corresponds to the relative configuration (RS)-(SR) of the two central carbon atoms according to the Kahn-Ingold-Prelog convention.

The invention relates also to processes for the manufacture of the above-defined compounds according to the invention, and to pharmaceutical compositions that contain these compounds as active ingredient, and to corresponding manufacturing processes by which such compositions are manufactured by non-chemical methods. The invention relates furthermore to the therapeutic use of the above-defined compounds and pharmaceutical compositions, especially in alleviating and curing those pathological conditions in which the pronounced leucotriene-antagonistic activity and/or phospholipase-inhibiting activity of the compounds according to the invention can be utilized, such as in the case of allergies of various types, especially in the case of asthma, and in the case of inflammation, especially of the skin and the mucosa.

A few years ago it was demonstrated (cf. H. R. Morris et al. Nature 285, 1045-1106 (May 1980) and L. Oerning, S. Hammarström and B. Samuelsson: Proc. Natl. Acad. Sci. USA 77 (4), 2014-2017 (1980)) that leucotrienes, especially leucotriene C and D, as a primary cause of a hypersensitivity reaction having immediate onset, are in all probability responsible for bronchial constriction in asthma.

The basic structural framework of leucotrienes in general is formed by a polyunsaturated linear icosanic acid which carries characteristic substituents in the 1-, 5- and 6-positions, as is shown by the formula below for the mentioned most important representatives:

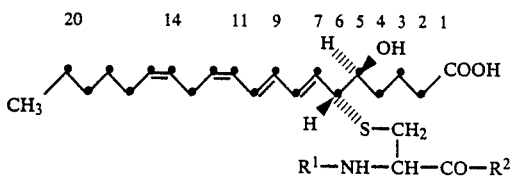

LTC-4: $R^1$=HOCOCH($NH_2$)$CH_2CH_2$CO—; $R^2$=—NHCH$_2$COOH

LTD-4: $R^1$=H—; $R^2$=—NHCH$_2$COOH

LTE-4: $R^1$=H—; $R^2$=—OH

[Here, the spatial representation is to be understood as follows: the entire olefinic chain lies in the plane of representation and the valency lines indicated by arrows extend above the plane of representation whilst the broken lines extend below the plane.]

In their physiological properties, leucotrienes are in general distinguished by the fact that they cause a marked contraction of smooth muscle of the most varied kinds. From the standpoint of health such an effect is generally undesirable, and accordingly the search for suitable leucotriene antagonists is in the forefront of research in this field.

Surprisingly, it has now been shown that although the compounds of the formula I according to the invention have several structural features in common with known leucotrienes, they have a pronounced antagonistic effect on the latter. Thus, in various test arrangements in vitro they have a clear leucotriene-antagonistic action.

For example, in the tested concentration range of approximately from 0.1 to 25 μmol/l they inhibit the contraction of a smooth muscle induced by leucotriene-D$_4$ (LTD$_4$ - see above). This so-called LTD$_4$-antagonism is demonstrated experimentally, for example, in the following manner: In segments taken from the ileum of a guinea pig weighing 300-400 g and incubated in an organ bath in Tyrode's solution at 38° C. whilst gassing with a mixture of 95% oxygen and 5% carbon dioxide at a load of 1 g, contractions are triggered with synthetic leucotriene-D$_4$ (in the form of a potassium salt) and isotonically registered. The extent of inhibition by the test substance is ascertained after a preliminary incubation of 2 minutes and evaluated as IC$_{50}$, that is to say the concentration that reduces the test contraction by 50%. The LTD$_4$antagonism can also be demonstrated in vivo by a bronchoconstriction standard test on guinea pigs with aerosol administration. (The description of the test method is appended after the Examples.)

Surprisingly, compounds of the formula I also have a pronounced inhibiting effect on other physiologically important enzyme systems. For example, the inhibition of phospholipase $A_2$ from human leucocytes was observed in the tested concentration range of approximately from 0.5 to 50 $\mu$mol/l. (The experimental arrangement for this determination is described in detail in the appendix after the Examples.) Similarly, the inhibition of phospholipase C from human thrombocytes was observed in the tested concentration range of approximately from 1 to 100 $\mu$mol/l (for the experimental arrangement see the appendix after the Examples).

The antiallergic and antiinflammatory properties indicated in vitro by these methods are also confirmed in animal tests in vivo. For example, the local antiinflammatory activity can be demonstrated, for example, according to the method developed by G. Tonelli and L. Thibault [Endocrinology 77, 625 (1965)], by inhibition of the oedema induced by croton oil in the ears of normal rats in a dosage range of from approximately 1 to approximately 100 mg/ml.

Owing to these valuable pharmacological properties, the compounds of the formula I according to the invention can be used therapeutically in all cases where the allergogenic action of leucotrienes leads to pathological conditions and is to be reduced or eliminated. Consequently, they can be used, for example, for the treatment of allergic conditions and diseases, such as, especially, asthma, but also hay fever and obstructive lung diseases, including cystic fibrosis. Similarly, owing to their antiinflammatory activity, they are suitable as inflammation-inhibiting agents, especially as external (topical) skin anti-phlogistic agents for the treatment of inflammatory dermatoses of any kind, such as in the case of mild skin irritations, contact dermatitis, exanthema and burns, and as mucosa anti-phlogistic agents for the treatment of inflammations of the mucosa, for example the eyes, nose, lips, mouth and genital or anal region. They can also be used as sun-screening agents. In addition, the high inhibiting activity on various blood factors suggests the possibility of therapeutic use of the compounds of the formula I in the thrombosis and blood coagulation indication range.

As already mentioned above, there is a general analogy between the structure of the compounds of the formula I according to the invention and that of leucotrienes, especially in the preferred trans-configuration of the vicinal S- and O-atoms mentioned at the beginning and the total structure of the mercaptoalkanoic acid residue (M) (especially in its typical form of a cysteine peptide). They differ, however, from leucotrienes essentially in that they lack the characteristic terminal carboxy group in the linear radical (L), which group may optionally be replaced by various other functional groups, such as, especially, halogen atoms. Also, in contrast to leucotrienes, the number, character and spatial arrangement of the multiple bonds are not critical, since the latter may be missing or may be replaced by phenylene radicals. Also, the total length of the radical (L) is, within wide limits, incidental to the activity, and neither the absolute nor even the relative configuration of the two above-discussed asymmetric carbon atoms is critical for the activity, as can be demonstrated, for example, with active 5(R),6(S)-epimers, which by comparison with natural leucotrienes have reverse absolute configuration of the carbon atoms 5 and 6 of the hydrocarbon chain (L).

The number of methylene groups indicated by the symbol a in the formula I defined at the beginning is preferably 1 or 2. Of the preferred meanings of $R^o$ in formula I there may be mentioned especially hydrogen, and also $C_{1-4}$-alkanoyl, such as acetyl.

In the above-defined formula I, the symbol $R^1$ preferably represents an alkyl group, such as methyl, propyl and, especially, ethyl, that is unsubstituted or substituted at the terminal C-atom by chlorine or, especially, fluorine, for example chloromethyl or fluoromethyl, or a corresponding $\omega$-hydroxyalkyl group, such as, especially, $\beta$-hydroxyethyl, wherein the hydroxy group may be present not only in free form but also in esterified form. An esterified hydroxy group is preferably esterified by the radical of an aliphatic or aromatic carboxylic acid having a maximum of 12 carbon atoms, such as benzoic acid or, especially, a $C_{1-7}$-alkanoic acid, especially acetic acid. Trifluoromethyl is preferred as a perfluoroalkyl group.

The aliphatic radical represented by the symbol $R^2$ is preferably a linear radical, for example an alkyl radical, consisting of from 5 to 15, preferably from 7 to 12, carbon atoms, such as, especially, heptyl, nonyl, undecyl and dodecyl, or a corresponding mono- or polyunsaturated radical that carries one, two or three multiple bonds, such as triple bonds and, especially, doulle bonds, in the cis- or trans-configuration as desired, in any combination. These multiple bonds are preferably as close as possible to the sulphur atom, that is to say in the $\alpha,\beta$-position to the sulphur-carrying carbon atom or conjugated with the vinylene radical represented by A. Preferred radicals $R^2$ of this type are, for example, 1-alkenyl, 1,3-alkadienyl and 1,3,6-alkatrienyl radicals, such as, especially, 1-heptenyl, 1-octenyl, 1-nonenyl, 1-decenyl, 1-undecenyl and 1-dodecenyl or 1,3-octadienyl, 1,3-decadienyl, 1,3-dodecadienyl and 1,3,6-dodecatrienyl, in which all of the double bonds can each individually be in cis- or trans-configuration and can form any combination.

The vinylene radical represented by the symbol A in formula I may be in the cis- or trans-configuration.

Symbol B in formula I may preferably represent a single bond; if, however, with this meaning of B, at the same time there is no halogen atom present in the radical $R^1$, then A must represent the ethylene radical. Symbol B may also preferably represent a phenylene radical, such as m- and especially o- or p-phenylene, which may be alkylated by one or more $C_{1-4}$-alkyl radicals, especially methyl radicals, having a maximum of 6 C-atoms in total, but is preferably unsubstituted. If B represents phenylene, A preferably represents a single bond.

The symbol $R^3$ defined in formula I given at the beginning forms, together with the adjacent carbonyl group —CO—, a free or functionally modified carboxy radical; if $R^3$ represents hydroxy, it forms with the carbonyl group the carboxy radical of a free carboxylic acid; if $R^3$ represents an alkoxy group, especially one with a maximum of 7 carbon atoms, especially methoxy, it completes a carboxylic acid ester; and, if $R^3$ represents an amino group, it belongs to the amide bond of a carboxamide or, if the amino group is suitably substituted, of a peptide. In that latter case, the substituted amino group is the fundamental element of an amino acid, such as of an $\alpha$-aminocarboxylic acid and especially of an $\alpha$-amino-$C_{2-7}$-alkanoic acid, preferably one that occurs naturally, such as leucine, valine, alanine (especially in the "natural" L-form) and, especially, glycine. The carboxy group of those amino acids can then in turn be in the form of free carboxy or may be functionally modified in the above-defined manner as an ester group, such as, especially, a $C_{1-7}$-alkoxycarbonyl group, or the carboxamido group $—CONH_2$. Such preferred meanings of the symbol $R^3$ thus correspond to the partial formula

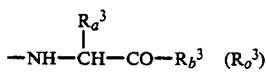

in which $R_a^3$ represents a $C_{1-5}$-alkyl group or, preferably, hydrogen, and $R_b^3$ represents hydroxy, $C_{1-7}$-alkoxy or the primary amino group $NH_2$.

The symbol $—X—$ defined at the beginning can, on the one hand, represent a single C—C bond, and thus together with the adjacent groups form the residue of mercaptoacetic acid $—S—CH_2—CO—R^3$; in this case, of the above-mentioned meanings for $R^3$ hydroxy is especially preferred. On the other hand, $—X—$ can represent an aminomethylene group optionally acylated at the nitrogen atom, which group thus corresponds to the partial formula

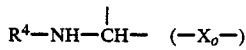

in which $R^4$ represents hydrogen or the acyl radical of a carboxylic acid, such as an aliphatic or aromatic carboxylic acid with a maximum of 12 carbon atoms, especially an unsubstituted or substituted, preferably linear, $C_{1-5}$-alkanoic acid. Of substituted alkanoic acids of this kind the following, especially, may be mentioned: on the one hand mono- or, preferably, polyhalogenated, especially chlorinated or fluorinated, $C_{1-5}$-alkanoic acids, such as, especially, trifluoroacetic acid, and, on the other hand, mono- and di-basic amino acids including monoamides of the latter, especially α-amino acids of the type that occur naturally as building blocks of peptides and especially in L-form; of these attention is drawn, for example, to glutamic acid, which preferably acylates the amino group with its γ-carboxy group. According to this representation the symbol $R^4$ preferably represents hydrogen, trifluoroacetyl or γ-glutamyl of the formula $HOCOCH(NH_2)CH_2CH_2CO—$; in the latter the free carboxy group may be in the form of a salt.

Preferably, the above-characterised aminomethylene group, together with the adjacent symbols, forms an optionally acylated cysteine residue of the partial formula

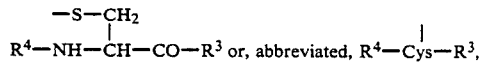

in which $R^3$ and $R^4$ have the above-mentioned general and preferred meanings, the L-cysteinyl residue with the naturally occurring configuration at the asymmetric carbon atom being preferred. In this case $R^3$ preferably represents hydroxy, $C_{1-4}$-alkoxy or a glycine residue bonded at the nitrogen atom and optionally esterified by a $C_{1-4}$-alkanol, and $R^4$ represents especially hydrogen, trifluoroacetyl or γ-glutamyl (also in salt form).

Most of the compounds of the formula I, depending on their individual character, can also be in the form of salts. Those that have adequate acidity, such as especially those having free carboxy groups, can form salts with bases, such as, especially, inorganic bases, preferably physiologically tolerable alkali metal salts, especially sodium and potassium salts. Those of the compounds of the formula I that have adequate basicity, such as esters and amides of amino acids, can be in the form of acid addition salts, especially physiologically tolerable salts, with customary pharmaceutically acceptable acids; of the inorganic acids there may be mentioned especially hydrohalic acids, such as hydrochloric acid, and sulphuric acid and phosphoric or pyrophosphoric acid, and of the organic acids there may be mentioned especially sulphonic acids, for example aromatic sulphonic acids, such as benzene- or p-toluenesulphonic acid, embonic acid and sulphanilic acid, or lower alkanesulphonic acids, such as methanesulphonic, ethanesulphonic, hydroxyethanesulphonic acid and ethylenedisulphonic acid, but also aliphatic, alicyclic, aromatic or heterocyclic carboxylic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic and p-aminosalicylic acid, as well as ascorbic acid. Compounds of the formula I that contain both basic and acidic functional groups, such as free carboxy and amino groups, can also be in the form of internal salts.

Attention is drawn in particular to compounds of the formula I in which the entire residue (M) of the mercaptoalkanecarboxylic acid mentioned at the beginning is represented by one of the following formulae, wherein the amino acid residues of the "natural" L-series are preferred:

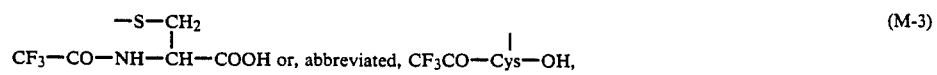

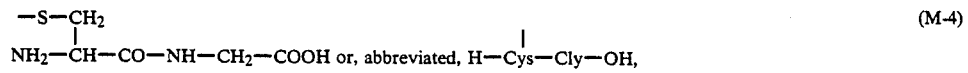

$$\underset{NH_2-CH-COOH}{-S-CH_2} \text{ or, abbreviated, } H-\overset{|}{C}ys-OH \quad (M-5)$$

and $$-S-CH_2-COOH. \quad (M-6)$$

Also included are corresponding compounds in which th carboxy groups are present in the form of a primary amide or $C_{1-4}$-alkyl ester, or especially in the form of a salt, preferably an alkali metal salt.

Especially preferred are compounds of the formula I in which the general symbols have the following especial meanings:

a is an integer from 2 to 5, $R^o$ represents hydrogen, $R^1$ represents chloromethyl, fluoromethyl or, especially, methyl, $R^2$ represents an alkyl group having from 5 to 15, preferably from 8 to 12, carbon atoms, A represents a single bond, B represents a phenylene group, such as, especially, o- or p-phenylene, $R^3$ represents hydroxy or —Gly—OH (that is to say, a radical of the formula —NH—CH$_2$—COOH) and —X— represents methylene or the above-defined radical —$X_o$— in which $R^4$ represents trifluoroacetyl and the trifluoroacetylamino group has the same configuration as in natural L-cysteine; most especially preferred of these compounds are those in which the above-defined residue, indicated by M, of the mercaptoalkanoic acid corresponds to the formula —S—CH$_2$—CH$_2$—COOH or the above formula M-2. All of these preferred compounds may be in the form of a free acid or, especially, in salt form, such as in the form of a physiologically tolerable salt, for example a sodium or potassium salt.

Attention is drawn more especially to the compounds of the formula I described in the Examples.

The thioethers according to the invention can be manufactured in a manner known per se, for example in the following manner: an aliphatic cis- or, preferably, trans-epoxide having a minimum of 11 carbon atoms and corresponding to the residue (L) defined at the beginning, especially of the formula $$R^2-B-A-CH\overset{O}{\underset{\diagdown}{-}}CH-(CH_2)_a-R^1 \quad (II)$$

in which a, A, B, $R^1$ and $R^2$ have the meanings given above and in which, preferably, the two hydrogen atoms at the oxirane ring are trans-orientated with respect to one another, and in which a hydroxy group, if present, can be in a protected form, is reacted with a mercaptoalkanecarboxylic acid corresponding to the above-defined residue (M), especially of the formula $$HS-CH_2-X-CO-R^3 \quad (III)$$

in which $R^3$ and —X— have the meanings given above, in which acid an amino group, if present, can be in a protected form, or with a salt thereof or a derivative thereof having a modified carboxy group, and, if necessary or desired, a resulting compound of the formula I in which $R^o$ represents hydrogen is acylated to a corresponding compound in which $R^o$ represents $C_{1-7}$-alkanoyl, and/or the protecting groups of the hydroxy and/or amino group are removed, and/or a compound present in the form of an ester is hydrolysed to the free acid or a salt thereof, and, if desired, a resulting free compound with salt-forming properties is converted into a salt thereof or a resulting salt is converted into a free compound.

The reaction is carried out under conditions known per se at temperatures of from approximately −20° C. to approximately +50° C., preferably at room temperature, and especially in a basic medium, for example in the presence of an amine, especially a tertiary aliphatic, arylaliphatic or saturated heterocyclic amine, such as trialkylamine (for example triethylamine or ethyldiisopropylamine), dialkylbenzylamine (for example N,N-dimethylbenzylamine), N,N-dialkylaniline (for example N,N-dimethylaniline) or N-methyl- or N-ethyl-piperidine or N,N'-dimethylpiperazine. Usually, the reaction is carried out in an inert organic solvent, such as a lower alkanol, for example methanol or ethanol.

The acylation of the hydroxy group formed in the main process, which may be carried out subsequently and which leads to compounds of the formula I in which $R^o$ represents $C_{1-7}$-alkanoyl, can be carried out in a manner known per se, for example by treatment of the primary product in which $R^o$ represents hydrogen with the desired acid, such as, for example, formic acid, or with a suitable reactive acid derivative, especially a halide (preferably chloride), symmetric anhydride, mixed anhydride (especially one with trifluoroacetic acid) or ketene. There may be used as reaction medium, for example, excess acylating agent, and also neutral, non-acylatable organic solvents, such as hydrocarbons (for example pentane, hexane, cyclohexane), halogenated hydrocarbons (for example methylene chloride, chloroform), ethers (for example diethyl ether, ethylene glycol dimethyl ether, tetrahydrofuran, dioxan), acid esters (for example ethyl acetate) and acid amides (for example acetamide, dimethylformamide); and optionally also non-acylatable organic bases of differing basicity, such as heteroaromatic bases (for example pyridine, collidine, quinoline), tertiary amines (for example triethylamine, N-ethylpiperidine, N-methylmorpholine, N,N'-dimethylpiperazine) or 1,5-diazabicyclo[5.4.0]-undec-5-ene; alternatively the operation is carried out with advantageous combinations of all of these solvents. The reaction temperature may be in the range of approximately from −70° to the boiling temperature of the mixture, preferably between approximately −20° and approximately +30° C.

The acylation is preferably carried out after the main reaction, that is to say with products of the process in which any amino and/or hydroxy groups that may be present are still in protected form. (The removal of the groups used for the temporary protection is then effected according to general methods known per se.) It is, however, also possible to carry out the acylation at any later stage, but in such a case all other free hydroxy groups and amino groups are at the same time substituted with the same acyl.

If a free hydroxy group is present in the starting material, especially in the substituent $R^1$ in the formula II, it can be in a protected, such as etherified, form during the reaction. Preferred are readily removable, especially acidolytically removable, hydroxy-protecting groups, such as are generally well known, especially from peptide and steroid chemistry; of these, protecting groups of the tert.-butyl ether type and, especially, tetrahydropyranyl ether (THP ether) type are especially preferred. When the main reaction (that is to say condensation of the epoxide with the mercaptocarboxylic acid) is complete, these protecting groups can be removed in generally known manner, thus freeing the hydroxy group, for example by treatment with an organic acid, such as formic acid, acetic acid, oxalic acid or trifluoroacetic acid, or a mixture thereof, and optionally in the presence of water and/or inert organic solvents, such as lower alkanols (for example methanol or ethanol) and cyclic ethers (such as tetrahydrofuran or dioxan).

If the mercaptocarboxylic acids used as starting material contain a free amino group, then this can preferably be in a protected, such as especially an acylated, form during the main reaction. Preferably, readily removable, especially acidolytically removable, amino-protecting groups are used, such as are generally well known, especially in peptide chemistry, as are the conditions for their removal. Of the amino-protecting groups, however, the trifluoroacetyl group is to be given special mention: when the main reaction is complete this group can remain in the end product according to the invention or, if desired, can subsequently be removed. The removal of the N-trifluoroacetyl group is carried out, as is known, preferably by hydrolysis, especially under basic conditions, such as with alkali metal carbonates (for example sodium or potassium carbonate) or dilute alkali hydroxide solutions (for example sodium or potassium hydroxide) in the presence of water in a water-miscible organic solvent, such as a lower alkanol (for example methanol or ethanol) or cyclic ether (for example tetrahydrofuran or dioxan) at temperatures of approximately from 0° to 80° C., preferably at a slightly elevated temperature of approximately from 50° to 60° C. If ester groups are present in the product to be hydrolysed, such as an acylated hydroxy group in the hydroxyalkyl radical $R^1$ or an esterified carboxy group in the mercapto acid residue (M), then under these conditions they are hydrolysed at the same time.

In the main reaction (condensation with epoxide) the mercaptocarboxylic acid is used especially in the form of its ester, preferably a $C_{1-4}$-alkyl ester (such as the methyl or ethyl ester); if the end product according to the invention is desired in the form of a free acid or its salt, then the resulting ester must be hydrolysed. The hydrolysis is carried out under the customary conditions, for example those described hereinbefore for the base-catalysed hydrolytic removal of the N-trifluoroacetyl group. It is, however, also possible selectively to remove the ester group with retention of the N-trifluoroacetyl group using milder conditions, such as especially at low temperature (preferably at room temperature), with an equivalent stoichiometric amount of alkali, and using a shorter reaction time, optionally with analytical monitoring, for example by thin layer chromatography, but in the course of this operation an acylated hydroxy group is generally removed at the same time.

Starting materials for the condensation process according to the invention are either known per se or can be obtained in a manner known per se according to known analogy processes. Thus, for example, the important mercaptocarboxylic acids of the formula III have been described (cf. for example, E. J. Corey et al.: Tetrahedron Letters 1980, 3143), and other analogous acids can be obtained in the same manner starting from corresponding known starting materials. For the manufacture of cysteine derivatives, analogous known cystine compounds are advantageously used and subjected to the customary reductive cleavage of the disulphide bond, or are processed as cysteine derivatives with a mercapto group that is suitably protected, for example by trityl or acetylaminomethyl.

The cis- or preferably trans-epoxide used as starting material, for examle that of the above-defined formula II, can be manufactured especially by means of the same processes as those used in the synthesis of leucotrienes. For example, in a typical general method of synthesis, there is used as starting material a saturated aliphatic aldehyde (alkanal) of the formula

in which a and $R^1$ have the meanings given above, a free hydroxy group that may be present in the radical $R^1$ being protected in the form of an ether, for example one of the forms described above. This compound is condensed with formylmethylenetriphenylphosphorane (or an equivalent reagent), resulting in the corresponding α,β-unsaturated aldehyde, 2-trans-alkenal, of the formula

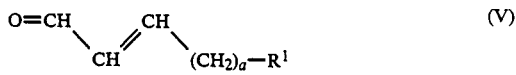

in which a and $R^1$ have the meanings given above and a free hydroxy group that may be present in the radical $R^1$ is protected in the form of an ether or ester. This compound is then epoxidised in a manner known per se, preferably under weakly alkaline conditions (for example in the presence of alkali carbonates), with aqueous hydrogen peroxide, resulting in a trans-epoxide, 2(RS),3(SR)-epoxy-alkanal of the formula

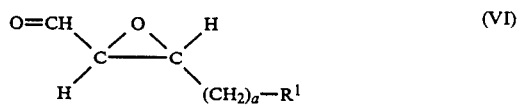

in which a and $R^1$ have the meanings given above and a free hydroxy group that may be present in the radical $R^1$ is protected in the form of an ether. This epoxyaldehyde can be condensed to the desired trans-unsaturated epoxide, for example to that of the above-defined formula II in which a free hydroxy group that may be present in the radical $R^1$ is in protected etherified form and A represents the vinylene radical, by condensation with a corresponding known benzylidene or alkylidene triphenylphosphorane. For polyunsaturated epoxides, for example those of the formula II in which $R^2$ has one or more double bonds, there is an indirect alternative: instead of the Wittig reaction with an ylidene phosphorane unsaturated in its chain, the aldehyde IV is first lengthened by 4 carbon atoms with γ-triphenylphosphoranylidenebutyraldehyde (4-triphenylphosphoranylidenebutanal), epoxidised and only the resulting 6(RS),7(RS)-epoxy-2-alkenal is condensed with a single saturated alkylidene triphenylphosphorane or a less complicated benzylidene or alkenylidene triphenylphosphorane to the desired epoxide (for example one of the formula II). In the case of epoxides of the formula II in which A represents a single bond and B represents phenylene, the aldehyde IV is reacted with a corresponding benzylidene triphenylphosphorane and subsequently epoxidised. In this case, however, usually a mixture of cis- and trans-styryl derivatives is formed, which must either be separated into the two individual isomers, or results in a mixture of the two isomeric epoxides from which then, in the main process, four stereoisomers may be formed.

If individual diastereoisomers are desired, then advantageously, at any stage, an individual diastereoisomer of a starting material can be used or a diastereoisomer can be formed preferentially from a racemic or optically inactive starting material by stereoselective reaction conditions or optically active reagents, or racemic diastereoisomeric mixtures can be separated by physical separation methods, optionally with the use of optically active auxiliaries, into optically individual diastereoisomers.

From the stereochemical point of view, however, both the condensation according to the invention of the formation components II and III, and the preparation of the starting materials, are especially carried out using in each case stereochemically uniform starting materials, carrying out the reactions as far as possible stereoselectively, for example by using optically active reagents and/or auxiliaries, and isolating stereochemically uniform products from the reaction mixtures directly after the reaction. Thus, for example, in the manufacture of the unsaturated starting materials, isomers with cis- and trans-double bonds that may be formed are immediately separated from one another, for which purpose the customary physical separation methods, such as, especially, chromatography, are suitable. In the main reaction, especially the epoxide of the formula II is used as an individual trans-stereoisomer, but in racemic form (which is the form normally obtained by the epoxidation of an olefin); the mercaptoalkanoic acid of the formula III, if it is optically active, is preferably used in the form of an individual optical antipode (which is the usual case especially with cysteine and its derivatives)—this measure makes it possible for the two optically active diastereoisomers formed to be separated from one another simply by customary physical methods, such as chromatography; if an optically inactive mercaptoalkanoic acid is used, in order to obtain individual optically active products it is absolutely necessary to use the methods of cleaving into antipodes by means of optically active auxiliaries, such as, for example, the formation of salts with optically active bases. All suitable separation processes are known per se and can also be repeated or expediently combined with each other.

Owing to the close relationship between the novel compounds in free form and in the form of their salts, there are accordingly to be understood hereinbefore and hereinafter by the free compounds or their salts also the corresponding salts or free compounds, respectively.

The invention relates also to those embodiments of the process according to which a compound obtainable as intermediate at any stage of the process is used as starting material and the remaining steps are carried out, or a starting material is used in the form of a salt or is formed under the reaction conditions.

The invention relates also to the novel starting materials and intermediates produced in the processes according to the invention and the initial stages thereof.

The starting materials and the reaction conditions are preferably so selected that the compounds listed hereinbefore as being especially preferred are obtained.

The present invention relates also to pharmaceutical compositions and medicaments that contain one of the compounds of the formula I according to the invention or a pharmaceutically acceptable salt thereof. The pharmaceutical compositions according to the invention are especially those which are designed for local administration and, especially, for inhalation administration, for example in the form of an aerosol, a micropulverised powder or a finely sprayed solution, to mammals, especially man, and which contain the active ingredient on its own or together with a pharmaceutically acceptable carrier.

Pharmaceutical preparations for topical and local use are, for example for the treatment of skin, lotions and creams that contain a liquid or semi-solid oil-in-water or water-in-oil emulsion, and ointments (these preferably containing a preservative. Suitable preparations for treatment of the eyes are eyedrops that contain the active compound in aqueous or oily solution, and eye ointments that are preferably manufactured in sterile form. Suitable preparations for the treatment of the nose are aerosols and sprays (similar to those described hereinafter for the treatment of the respiratory tract), coarse powders that are administered by rapid inhalation through the nostrils and, especially, nose drops that contain the active compound in aqueous or oily solution; suitable preparations for local treatment of the buccal cavity include lozenges that contain the active compound in a composition formed generally from sugar and gum arabic or tragacanth to which flavourings can be added, and pastilles that contain the active ingredient in an inert composition, for example consisting of gelatine and glycerine or sugar and gum arabic.

Suitable pharmaceutical compositions for administration in the form of aerosols or sprays are, for example, solutions, suspensions or emulsions of the active ingredient of the formula I according to the invention with a suitable pharmaceutically acceptable solvent, such as, especially, ethanol and water, or a mixture of such solvents. Depending on the requirements the compositions can also contain other pharmaceutical adjuncts, such as non-ionic or anionic surfactants, emulsifiers and stabilisers, as well as active ingredients of other kinds, and especially advantageously can be mixed with a propellant gas, such as an inert gas under elevated pressure, or, especially, with a readily volatile liquid that preferably boils under normal atmospheric pressure below the usual room temperature (for example between approximately $-30°$ and $+10°$ C.), such as an at least partially fluorinated polyhalogenated lower alkane, or with a mixture of such liquids. Such pharmaceutical compositions, which are predominantly used as intermediates or as stock mixtures for the manufacture of the corresponding medicaments in finished form, contain the active ingredient usually in a concentration of from approximately 0.1 to approximately 10%, especially from approximately 0.3 to approximately 3%, by weight. For the manufacture of medicaments in finished form, such a pharmaceutical composition is introduced into suitable containers, such as small bottles and pressurised bottles, which are provided with a spraying device or valve suitable for such purposes. The valve is preferably constructed as a metering valve which, on operation, releases a predetermined amount of liquid corresponding to a predetermined dose of the active ingredient. When manufacturing the finished medicament form, it is also possible for corresponding amounts of the pharmaceutical composition, in the form of stock solution, and of the propellant to be introduced separately into the containers and to be mixed only then. The dosage of the active ingredient of the formula I to be administered and the frequency of administration depend on the particular activity and on the duration of action of the individual compounds, on the severity of the illness to be treated and its symptoms, and on the sex, age, weight and individual responsiveness of the mammal to be treated. On average, the recommended daily dose of a compound of the formula I according to the invention for a mammal weighing 75 kg (especially man) is likely to lie within the range of from approximately 10 to approximately 500 mg, preferably from approximately 25 to approximately 250 mg, administration advantageously being effected in several doses per day as required.

The invention relates also to the use of the active ingredients of the formula I according to the invention for alleviating or curing pathological conditions and/or symptoms of the body of a mammal, especially man, that are attributable to the allrgogenic action of leucotrienes and occur especially in the case of asthma. This use and the corresponding method of treatment is characterised by treating the affected body or part of the body with an antiallergically effective amount of a compound of the formula I on its own or in the form of a medicament, especially a pharmaceutical composition designed for inhalation. There is to be understood by "an antiallergically effective amount" that amount of the active ingredient which is sufficient to bring about significant inhibition of the contractions caused by leucotrienes.

The following Examples illustrate the present invention in more detail without limiting the scope thereof. All temperatures are quoted in degrees Celsius. The amino acids as formation components of the described compounds are in the "natural" L-form.

EXAMPLE 1

3-[S-4(RS),5(SR)-4-hydroxy-1,1,1-trifluoro-6-cis-icosen-5-ylthio]-propionic acid methyl ester A solution of 186 mg (1.55 mmol) of 3-mercaptopropionic acid methyl ester in 4 ml of methanol is added to a solution of 500 mg (1.44 mmol) of 4(RS),5(RS)-4,5-epoxy-1,1,1-trifluoro-6-cis-icosene and 0.62 ml (4.5 mmol) of triethylamine in 8 ml of methanol. The solution is stirred for 10 hours at room temperature under argon, the solvent is evaporated off in vacuo, and the residue is purified by chromatography on silica gel with dichloromethane. The title compound is obtained in the form of a light-yellow oil.

IR ($CH_2Cl_2$) 2940, 2870, 1745, 1445, 1370, 1300, 1250, 1225, 1150 cm$^{-1}$.

By treating the same amount of the above-mentioned epoxide with 446 mg (1.55 mmol) of N-[N-trifluoroacetylcysteinyl]-glycine methyl ester under analogous conditions, crude N-[S-4(RS),5(SR)-4-hydroxy-1,1,1-trifluoro-6-cis-icosen-5-yl-N-trifluoroacetylcysteinyl]-glycine methyl ester is obtained, which is purified by chromatography on silica gel using as eluant a (19:1) mixture of chloroform/methanol.

IR ($CH_2Cl_2$) : 2940, 2870, 1760, 1740, 1700, 1530, 1220, 1180 cm$^{-1}$.

The epoxide used as starting material can be manufactured as follows:

(a) A solution of 12.6 g (0.1 mol) of 4,4,4-trifluorobutanal [T. Fuchikami and I. Ojima, J. Am. Chem. Soc. 104, 3527 (1982)] and 30.4 g (0.1 mol) of formylmethylenetriphenylphosphorane (see Tripett and D. M. Walker, J. Chem. Soc. 1961, 1266] in 200 ml of dichloromethane is heated under reflux for 24 hours under argon. The red solution is freed of solvent at room temperature in vacuo, and the residue is stirred thoroughly with ether/hexane (1:1). The solid portion is filtered off and subsequently washed three times with ether/hexane (1:1). The filtrate is concentrated by evaporation in vacuo and the residue is chromatographed with dichloromethane on silica gel. The product is eluted in the second fraction ($R_f=0.4$). 6,6,6-Trifluoro-2-trans-hexenal is obtained in the form of a light-yellow oil.

IR ($CH_2Cl_2$): 3070, 2960, 2880, 2620, 1700, 1650, 1395, 1250, 1150 cm$^{-1}$.

(b) 12.7 ml of 30% strength aqueous hydrogen peroxide and 425 mg of potassium carbonate are added to a solution of 5.3 g (0.035 mol) of 6,6,6-trifluoro-2-trans-hexenal in 400 ml of dichloromethane/methanol (1:1) and the whole is stirred for 12 hours at room temperature. 200 ml of phosphate buffer (pH=8) are added and the organic phase is separated off. The aqueous phase is extracted a further four times with 50 ml of dichloromethane each time. The combined organic phases are dried over sodium sulphate, filtered over a small amount of Florisil and concentrated by evaporation in vacuo at room temperature. 2(RS),3(SR)-2,3-epoxy-6,6,6-trifluorohexanal is obtained in the form of a light-yellow oil.

$^1$H-NMR (60 MHz, CDCl, $\delta$ in ppm): 1.25 (mc, 2H), 1.70–2.60 (m, 2H), 2.90–3.50 (m, 2H), 9.05 (d, 1H).

(c) 18.8 ml (0.030 mol) of a 1.6 molar solution of n-butyllithium in hexane are added dropwise while stirring, under an argon atmosphere, to a solution, cooled to 0° C., of 15.1 g (0.028 mol) of n-tetradecyltriphenylphosphonium bromide [E. J. Reist and P. H. Christie, J. Org. Chem. 35, 3521 (1970)] in 100 ml of tetrahydrofuran, the temperature being maintained at between 0° and 5° C. The red solution is then brought to room temperature and is stirred for a further 30 minutes. After being cooled to −25° C., a solution of 4.6 g (0.027 mol) of the 2(RS),3(SR)-2,3-epoxy-6,6,6-trifluorohexanal obtained according to (b) in 15 ml of tetrahydrofuran is added dropwise within a period of 15 minutes. The solution is allowed to warm to room temperature and is stirred for a further 2 hours. The solvent is evaporated off in vacuo and ether is added to the residue. The whole is left to stand for 24 hours at 0° C., the precipitated solid is filtered off and the solvent is evaporated off in vacuo. The residue is chromatographed on silica gel with dichloromethane/hexane (1:1, with 1% triethylamine). The desired 4(RS),5(RS)-4,5-epoxy-1,1,1-trifluoro-6-cis-icosene is obtained in the form of a pale yellow oil ($R_f=0.45$).

IR ($CH_2Cl_2$): 2940, 2870, 1460, 1390, 1300, 1250, 1155 cm$^{-1}$.

EXAMPLE 2

Sodium salt of 3-[S-4(RS),5(SR)-4-hydroxy-1,1,1-trifluoro-6-cis-icosen-5-ylthio]-propionic acid 9.5 ml (1.90 mmol) of 0.2N aqueous sodium hydroxide solution are added to a solution of 580 mg (1.24 mmol) of the methyl ester of the title compound (see Example 1) in 40 ml of methanol and the whole is stirred for 21 hours at room temperature. The solvent is evaporated off in vacuo at 30° C. and the residue is chromatographed with methanol/water (3:1) on a Merck Lobar ready-prepared column (size B, LiChroprep RP-8) at 10 bars. Evaporation of the eluant in vacuo yields the title compound in the form of a colourless resin. $^1$H-NMR (250 MHz, CD$_3$OD, δ in ppm): 0.9 (t, 3 H), 1.1–1.5 (m, 22 H), 1.56–1.86 (m, 2H), 2.04–2.5 (m, 4H), 2.4 (t, 2H), 2.7 (mc, 2H), 3.7 (mc, 2H), 5.4 (t, 1H), 5.6 (dt, 1H).

EXAMPLE 3

3-[1(RS),2(SR)-2-hydroxy-1-(2-nonylphenyl)-hexylthio]-propionic acid methyl ester A mixture of 3.02 g of 1(RS),2(RS)-1,2-epoxy-1-(2-nonylphenyl)-hexane, 3.5 ml of 3-mercaptopropionic acid methyl ester, 6 ml of triethylamine and 10 ml of methanol is stirred at room temperature for 7 days under argon. The reaction mixture is then concentrated by evaporation under reduced pressure at room temperature and the residue is purified by chromatography on silica gel with hexane and an increasing amount of ether. 3-[1(RS),2(SR)-2-hydroxy-1-(2-nonylphenyl)-hexylthio]-propionic acid methyl ester is obtained in the form of a colourless viscous oil.

IR (CHCl$_3$) 3580, 2960, 2930, 2860, 1730, 1440, 1250 cm$^{-1}$.

In analogous manner, but by analogous treatment of the above-mentioned epoxide with N-(N-trifluoroacetylcysteinyl)-glycine methyl ester, N-[S-1(RS),2(SR)-2-hydroxy-1-(2-nonylphenyl)-hex-1-yl-N-trifluoroacetylcysteinyl]-glycine methyl ester is obtained in the form of a viscous oil.

The 1(RS),2(RS)-1,2-epoxy-1-(2-nonylphenyl)-hexane used as starting material can be obtained as follows:

(a) 1-(2-nonylphenyl)-1-hexanol

A third of a solution of 11 g of 2-nonylbromobenzene [cf. EP-OL 0 123 543] in 15 ml of tetrahydrofuran is added to a mixture, stirred under an argon atmosphere, of 1.1 g of magnesium turnings, 8 ml of tetrahydrofuran and 3 drops of carbon tetrachloride, and the whole is heated at the boil, under reflux, for 30 minutes. The remainder of the solution of 2-nonylbromobenzene (cf. EP-OL 0 123 543) is then added dropwise over a period of 35 minutes and the reaction mixture is maintained under reflux for 2 hours. After dilution with 15 ml of tetrahydrofuran, the suspension is cooled to −10° C. and added in portions to a solution, cooled to −70° C., of 4.6 g of hexanal in 12 ml of tetrahydrofuran. After stirring for 1 hour at −70° C., 200 ml of saturated aqueous ammonium chloride solution are added to the reaction mixture, the organic layer is separated off and the aqueous layer is extracted three times with ether. The residue that remains after the combined ethereal extracts have been dried and concentrated by evaporation is purified by chromatography on silica gel with mixtures of petroleum ether with an increasing amount of methylene chloride, yielding the desired 1-(2-nonylphenyl)-1-hexanol in the form of a colourless oil.

IR (CH$_2$Cl$_2$) 3600, 2960, 2925, 2855, 1465 cm$^{-1}$.

(b) 1-(2-nonylphenyl)-1-trans-hexene

A mixture of 14.4 g of 1-(2-nonylphenyl)-1-hexanol, 2 g of toluene-4-sulphonic acid monohydrate and 250 ml of toluene is heated under reflux for 3 hours using a water separator. After cooling, the reaction mixture is washed twice with 10% strength (w/v) sodium bicarbonate solution and twice with water. The organic phase is dried over sodium sulphate and concentrated by evaporation in vacuo, and the residue is purified by chromatography on silica gel using hexene as eluant. The desired 1-(2-nonylphenyl)-trans-hexene is obtained in the form of a pale yellow oil.

IR (CH$_2$Cl$_2$): 2960, 2930, 2855, 1465, 970 cm$^{-1}$.

(c) 1(RS),2(RS)-1,2-epoxy-1-(2-nonylphenyl)-hexane 15.2 g of 85% strength 3-chloroperbenzoic acid are added to a solution of 13.6 g of 1-(2-nonylphenyl)-1-trans-hexene in 350 ml of methylene chloride and the whole is stirred for 3 hours at room temperature. The reaction mixture is diluted with methylene chloride and washed twice in each case with saturated sodium bicarbonate solution and water. The semi-solid residue that remains after the organic phase has been dried and concentrated by evaporation is suspended in hexane and filtered, and the filtrate is concentrated by evaporation under reduced pressure. Chromatographic purification of the crude product on silica gel with hexane/ether (97:3) yields the desired 1(RS),2(RS)-1,2-epoxy-1-(2-nonylphenyl)-hexane in the form of a colourless oil.

IR (CH$_2$Cl$_2$): 2960, 2930, 2860, 1470 cm$^{-1}$.

EXAMPLE 4

3-[1(RS),2(SR)-2-hydroxy-1-(2-dodecylphenyl)-pentylthio]-propionic acid methyl ester.

A mixture of 2.5 ml of 3-mercaptopropionic acid methyl ester, 4.2 ml of triethylamine, 3.3 g of 1(RS),2(RS)-1,2-epoxy-1-(2-dodecylphenyl)-pentane and 10 ml of methanol is stirred for 2 days under argon at room temperature. The reaction mixture is concentrated by evaporation in vacuo at 45° C. and the residue is purified by chromatography on silica gel with hexane/ethyl acetate (9:1). 3-[1(RS),2(SR)-2-hydroxy-1-(2-dodecylphenyl)-pentylthio]-propionic acid methyl ester is obtained in the form of a colourless viscous oil.

IR (CH$_2$Cl$_2$): 3580, 2930, 2855, 1735, 1465, 1440, 1360 cm$^{-1}$.

The 1(RS),2(RS)-1,2-epoxy-1-(2-dodecylphenyl)pentane used as starting material is obtained, for example, as follows:

(a) Cis- and trans-2-(1-dodecenyl)-bromobenzene 291.6 g of 2-bromobenzyltriphenylphosphonium bromide [cf. EP-OL 0 123 543] are added, in portions, within a period of 15 minutes to a suspension, cooled to 5° C., of 63.85 g of potassium tert.-butoxide in 2.8 liters of tetrahydrofuran under argon, the whole is stirred for one hour at 5° C., treated dropwise with a solution of 84.8 g of undecanal in 200 ml of tetrahydrofuran and stirred for 24 hours at room temperature. The reaction mixture is diluted with 2 liters of ether and washed twice with water. The semi-solid residue that remains after the organic phase has been dried and concentrated by evaporation is suspended in petroleum ethr and filtered, and the filtrate is concentrated by evaporation under reduced pressure. The crude product is purified by chromatography on silica gel with petroleum ether. Subsequent distillation of the pure fractions in vacuo yields a mixture of cis- and trans-2-(1-dodecenyl)-bromobenzene in the form of a colourless liquid, b.p. 132°–135° C./5.10$^{-3}$ mbar.

IR (CH$_2$Cl$_2$): 2925, 2855, 1465, 1020, 970 cm$^{-1}$.

(b) 2-dodecylbromobenzene 1.3 g of platinum oxide is added to a solution of 108.5 g of the mixture of cis- and trans-2-(1-dodecenyl)-bromobenzene obtained according to a) in 700 ml of ethanol and the whole is hydrogenated for 1 hour at normal pressure. The reaction mixture is then filtered through a glass fibre filter and concentrated by evaporation in vacuo. The residue is taken up in ether and washed twice in each case with saturated sodium bicarbonate solution and water. The residue obtained after the organic phase has been dried and concentrated by evaporation is distilled in vacuo. 2-dodecylbromobenzene is obtained in the form of a colourless liquid, b.p. 132°–135° C./8.10$^{-3}$ mbar.

IR (CH$_2$Cl$_2$): 2930, 2860, 1470, 1020 cm$^{-1}$.

(c) The last-mentioned product (71.6 g) is converted analogously to Example 3a) to the corresponding Grignard reagent, and condensed with 25.8 g of valeraldehyde to 1-(2-dodecylphenyl)-1-pentanol;

IR (CH$_2$Cl$_2$): 3600, 2930, 2860, 1470, 1040 cm$^{-1}$.

(d) The last-mentioned compound is dehydrated analogously to Example 3b) with 4-toluenesulphonic acid to 1-(2-dodecylphenyl)-1-trans-pentene;

IR (CH$_2$Cl$_2$): 2925, 2855, 1465, 970 cm$^{-1}$.

(e) There is obtained from 18.5 g of 1-(2-dodecylphenyl)-1-trans-pentene and 19.1 g of 3-chloroperbenzoic acid, analogously to Example 3(c), 1(RS),2(RS)-1,2-epoxy-1-(2-dodecylphenyl)-pentane.

IR (CH$_2$Cl$_2$): 2960, 2925, 2850, 1460, 905 cm$^{-1}$.

EXAMPLE 5

Sodium salt of 3-[1(RS),2(SR)-2-hydroxy-1-(2-nonylphenyl)-hexylthio]-propionic acid A mixture of 3.7 g of 3-[1(RS),2(SR)-2-hydroxy-1-(2-nonylphenyl)-hexylthio]-propionic acid methyl ester from Example 3, 108 ml of tetrahydrofuran and 56.8 ml of 0.2N aqueous sodium hydroxide solution is stirred for 16 hours at room temperature. The reaction mixture is concentrated by evaporation under reduced pressure at room temperature, and the residue is partitioned between methylene chloride and 2N hydrochloric acid. The organic phase is washed with water, dried over sodium sulphate, concentrated by evaporation in vacuo at 35° C. and the residue is purified by chromatography on silica gel with methylene chloride and an increasing amount of acetone. 0.1N aqueous sodium hydroxide solution is added to the resulting product until the pH value of the solution is approximately 7.2. Subsequent removal of the solvent yields the title compound;

IR (CH$_2$Cl$_2$): 3500, 2960, 2930, 2850, 1590, 1400 cm$^{-1}$.

In an analogous manner, but starting from N-[S-1(RS),2(SR)-2-hydroxy-1-(2-nonylphenyl)-hexyl-N-trifluoroacetylcysteinyl]-glycine methyl ester, the sodium salt of N-[S-1(RS),2(SR)-2-hydroxy-1-(2-nonylphenyl)-hexyl-N-trifluoroacetylcysteinyl]-glycine is obtained.

EXAMPLE 6

3-[1(RS),2(SR)-2-hydroxy-1-(2-dodecylphenyl)-pentylthio]-propionic acid

A mixture of 3.76 g of 3-[1(RS),2(SR)-2-hydroxy-1-(2-dodecylphenyl)-pentylthio]-propionic acid methyl ester from Example 4, 50 ml of methanol and 4.25 ml of 2N aqueous sodium hydroxide solution is stirred for 20 hours at room temperature under argon. The reaction mixture is then concentrated by evaporation under reduced pressure at 45° C. and the residue is partitioned between methylene chloride and 1N hydrochloric acid. The organic phase is dried over sodium sulphate and concentrated by evaporation in vacuo. The residue, purified by chromatography on silica gel with methylene chloride/methanol (9:1), yields the title compound in amorphous form.

IR (CH$_2$Cl$_2$): 3500, 3000 (broad), 2960, 2930, 2860, 1750, 1710, 1470, 1125 cm$^{-1}$.

EXAMPLE 7

N-[S-1(RS),2(SR)-2-hydroxy-1-(2-dodecylphenyl)-pentyl-N-trifluoroacetylcysteinyl]-glycine methyl ester A mixture of 3.3 g of 1(RS),2(RS)-1,2-epoxy-1-(2-dodecylphenyl)-pentane, 3.0 g of N-(N-trifluoroacetylcysteinyl)-glycine methyl ester (E. J. Corey et al., Tetrahedron Lett. 1980, 3193), 4.2 ml of triethylamine and 30 ml of absolute methanol is stirred for 20 hours at room temperature under argon. After filtration, the reaction mixture is concentrated by evaporation at room temperature in vacuo. Chromatography of the residue on silica gel with methylene chloride/acetone (98:2) yields the title compoun (mixture of diastereoisomers).

IR (CH$_2$Cl$_2$): 3580, 3390, 2960, 2925, 2845, 1745, 1725, 1685, 1525, 1210, 1170 cm$^{-1}$.

EXAMPLE 8

N-[S-1(RS),2(SR)-2-hydroxy-1-(2-dodecylphenyl)-pentyl-N-trifluoroacetylcysteinyl]-glycine 3.5 ml of 2N aqueous sodium hydroxide solution are added under argon to a mixture of 4.32 g of N-[S-1(RS),2(SR)-2-hydroxy-1-(2-dodecylphenyl)-pentyl-N-trifluoroacetylcysteinyl]-glycine methyl ester and 50 ml of methanol and the whole is stirred for 26 hours at room temperature. The reaction mixture is then concentrated by evaporation in vacuo and the residue is chromatographed on silica gel with methylene chloride/methanol (9:1). The pure fractions are concentrated by evaporation, taken up in ether and filtered. The mixture, comprising the title compound and the corresponding sodium salt, obtained after removing the solvent is partitioned between methylene chloride and 0.2N hydrochloric acid. Drying and concentration by evaporation of the organic phase yields N-[S-1(RS),2(SR)-2-hydroxy-1-(2-dodecylphenyl)-pentyl-N-trifluoroacetylcysteinyl]-glycine (mixture of diastereoisomers).

IR (CH$_2$Cl$_2$): 3340, 2930, 2855, 1730, 1680, 1530, 1220, 1175 cm$^{-1}$.

EXAMPLE 9:

3-[1(RS),2(RS)-2-hydroxy-1-(4-nonylphenyl)-hexylthio]-propionic acid methyl ester Under argon, 0.86 g of triethylamine and then 0.44 g of 3-mercaptopropionic acid methyl ester are added to 0.85 g of 1(RS),2(SR)-1,2-epoxy-1-(4-nonylphenyl)-hexane dissolved in 20 ml of methanol and the whole is stirred for 6 days at room temperature and concentrated by evaporation. Chromatography of the residue on silica gel with hexane/ethyl acetate (4:1) yields the title compound in the form of a colourless oil ($R_f=0.5$).

The 1(RS),2(SR)-1,2-epoxy-1-(4-nonylphenyl)hexane used as starting material can be manufactured, for example, as follows:

(a) 1-(4-nonylphenyl)-hex-1-ene (mixture of cis- and trans-isomers).

A suspension of 13.9 g of pentyltriphenylphosphonium bromide in 150 ml of tetrahydrofuran is cooled to $-20°$ under argon, 21.2 ml of 1.6M butyllithium solution in hexane are added within a period of 5 minutes and the whole is stirred for a further 30 minutes at $0°$–$10°$. 6 g of 4-nonylbenzaldehyde in 40 ml of tetrahydrofuran are added dropwise over a period of 30 minutes to the mixture, which has been cooled to from $-60°$ to $-70°$. The reaction mixture is allowed to warm spontaneously to $0°$–$10°$, stirred at this temperature for a further 45 minutes and concentrated by evaporation. The residue is taken up in hexane/ethyl acetate (1:) and filtered over silica gel. The filtrate is concentrated by evaporation and chromatographed on silica gel with hexane. The title compound (mixture of cis- and trans-isomers) is obtained in the form of a colourless oil, which is used directly in the next stage.

(b) 1,2-epoxy-1-(4-nonylphenyl)-hexane and separation into the individual cis- [1(RS),2(SR)-] and trans-[1(RS),2(RS)-] -isomers.

6.76 g of m-chloroperbenzoic acid (90% content) in 100 ml of dichloromethane are added to a solution of 6.32 g of 1-(4-nonylphenyl)-hex-1-ene (mixture of cis- and trans-isomers) from the preceding stage in 150 ml of dichloromethane while cooling to $0°$–$5°$, and the whole is stirred for 20 hours at $20°$. The rection mixture is washed in succession with 10% strength (w/v) sodium sulphite solution, 5% strength (w/v) sodium carbonate solution and 3 portions of water, dried over sodium sulphate and concentrated by evaporation. Chromatography of the residue on silica gel with hexane/ethyl acetate (19:1) yields in succession the trans-[1(RS),2(RS)-] and the cis-[1(RS),2(SR)-] -isomer in the form of colourless oils.

EXAMPLE 10:

3-[1(RS),2(SR)-2-hydroxy-1-(2-pentadecylphenyl)-pentylthio]-propionic acid methyl ester A mixture of 3.0 g of 1(RS),2(RS)-1,2-epoxy-1 -(2-pentadecylphenyl)-pentane, 3.6 ml of triethylamine, 1.6 ml of 3-mercaptopropionic acid methyl ester, 30 ml of methanol and 2 ml of tetrahydrofuran is stirred for 12 hours at room temperature under argon. The reaction mixture is then stirred for 4 hours at 45° C. By proceeding further in the manner described in Example 4, 3-[(RS),2(SR)-2-hydroxy-1-(2-pentadecylphenyl)pentylthio]-propionic acid methyl ester is obtained in the form of a yellowish viscous oil.

IR ($CH_2Cl_2$) :3580, 2960, 2920, 2850, 1735, 1465, 1435, 1360 $cm^{-1}$.

The 1(RS),2(RS)-1,2-epoxy-1-(2-pentadecylphenyl)-pentane used as starting material is obtained, for example, as follows:

(a) Cis- and trans-2-(1-pentadecenyl)-bromobenzene

The title compound is obtained in the form of a colourless liquid in a manner analogous to that described in Example 4a by using tetradecanal instead of undecanal.

IR ($CH_2Cl_2$): 2930, 2855, 1465, 1020, 970 $cm^{-1}$.

(b) 2-pentadecylbromobenzene

The title compound is obtained in the form of a colourless oil in a manner analogous to that described in Example 4b by using cis- and trans-2-( -pentadecenyl)-bromobenzene instead of cis- and trans-2-(1-dodecenyl)-bromobenzene. IR ($CH_2Cl_2$): 2920, 2850, 1470, 1020 $cm^{-1}$.

(c) 1-(2-pentadecylphenyl)-1-pentanol

The title compound is obtained in the form of a pale yellow oil in a manner analogous to that described in Example 3a using as starting materials 2-pentadecylbromobenzene and pentanal. IR ($CH_2Cl_2$): 3600, 2930, 2860, 1465 $cm^{-1}$.

(d) 1-(2-pentadecylphenyl)-1-trans-pentene

The title compound is obtained in the form of a colourless oil in a manner analogous to that described in Example 3b by using 1-(2-pentadecylphenyl)-1-pentanol instead of 1-(2-nonylphenyl)-1-hexanol.

IR ($CH_2Cl_2$): 2920, 2855, 1465, 965 $cm^{-1}$.

(e) 1(RS),2(RS)-1,2-epoxy-1-(2-pentadecylphenyl)pentane

The title compound is obtained in the form of a colourless oil in a manner analogous to that described in Example 3c by using 1-(2-pentadecylphenyl)-1-trans-pentene instead of 1-(2-nonylphenyl)-1-trans-hexene.

IR ($CH_2Cl_2$): 2960, 2930, 2860, 1465 $cm^{-1}$.

EXAMPLE 11:

3-[1(RS),2(SR)-2-hydroxy-1-(2-pentadecylphenyl)-pentylthio]-propionic acid

A mixture of 35 g of 3-[1(RS),2(SR)-2-hydroxy-1-(2-pentadecylphenyl)-pentylthio]-propionic acid methyl ester, 10 ml of methanol, 2 ml of tetrahydrofuran and 1.37 ml of 2N aqueous sodium hydroxide solution is stirred for 72 hours at room temperature under argon. Working up in the manner described in Example 6 yields the title compound in the form of pale yellow solids having a melting point of 28°–30° C.

IR ($CH_2Cl_2$): 3580, 3500, 3000 (broad), 2960, 2930, 2860, 1750, 1715, 1465 $cm^{-1}$.

EXAMPLE 12:

N-[S-1(RS),2(SR)-2-hydroxy-1-(3-nonylphenyl)-hexyl-N-trifluoroacetylcysteinyl]-glycine methyl ester; individual diastereoisomers 1(R),2(S) and 1(S),2(R)

The title compound is obtained in a manner analogous to that described in Example 3 but starting from 1(RS),2(RS)-1,2-epoxy-1-(3-nonylphenyl)-hexane and N-(N-trifluoroacetylcysteinyl)-glycine methyl ester; the title compound is separated into the diastereoisomers by chromatography on silica gel with hexane/ethyl acetate (3:2). The 1(R),2(S)-diastereoisomer, $[\alpha]_D^{20} = -78.8 \pm 3.1°$ (0.320% w/v in chloroform) is eluted before the 1(S),2(R)-diastereoisomer, $[\alpha]_D^{20} = +97.3 \pm 5.4°$ (0.185% w/v in chloroform).

The 1(RS),2(RS)-1,2-epoxy-1-(3-nonylphenyl)hexane used as starting material can be obtained as follows:

(a) 1-(3-nonylphenyl)-1-hexanol

The title compound is obtained in the form of a colourless oil in a manner analogous to that described in Example 3a but starting from 3-nonylbromobenzene (cf. EP-OL 0 123 543) and hexanal.
IR ($CH_2Cl_2$): 3590, 2920, 2930, 1465 cm$^{-1}$.

(b) 1-(3-nonylphenyl)-1-trans-hexane 1-(3-nonylphenyl)-1-hexanol is dehydrated analogously to Example 3b to form the title compound.
IR ($CH_2Cl_2$): 2960, 2920, 2850, 1470, 970 cm$^{-1}$.

(c) 1(RS),2(RS)-1,2-epoxy-1-(3-nonylphenyl)-hexane

Reaction of 1-(3-nonylphenyl)-1-trans-hexene analogously to Example 3c yields the title compound in the form of a light-yellow oil.

EXAMPLE 13:

Sodium salt of N-[S-1(S),2(R)-2-hydroxy-1-(3-nonylphenyl)-hexyl-N-trifluoroacetylcysteinyl]-glycine and its 1(R),2(S)-stereoisomer The corresponding ester is reacted analogously to Example 2 and the title compound is obtained, m.p. 145°–146° C.

The sodium salt of N-[S-1(R),2(S)-2-hydroxy-1-(3-nonylphenyl)-hexyl-N-trifluoroacetylcysteinyl]-glycine, m.p. 129°–130° C., is obtained in an analogous manner from the 1(R),2(S)-ester.

EXAMPLE 14:

3-[3(RS),4(SR)-4-hydroxy-1-(2-nonylphenyl)-1-trans-octen-3-ylthio]-propionic acid methyl ester A mixture of 822 mg of 3(RS),4(RS)-3,4-epoxy-1(2-nonylphenyl)-1-trans-octene, 0.5 ml of 3-mercaptopropionic acid methyl ester, 10 ml of methanol and 1 ml of triethylamine is stirred for 18 hours at room temperature under argon. Working up analogously to the manner described in Example 4 yields the title compound in the form of a colourless oil.
IR ($CH_2Cl_2$): 3580, 2960, 2930, 2860, 1735, 1465, 1435, 1360 cm$^{-1}$.

The 3(RS),4(RS)-3,4-epoxy-1-(2-nonylphenyl)-1-trans-octene used as starting material may be manufactured for example, in accordance with the following:

(a) 2-nonylbenzaldehyde

A third of a solution of 22 g of 2-nonylbromobenzene in 35 ml of tetrahydrofuran is added to a mixture, stirred under an argon atmosphere, of 3.4 g of magnesium turnings, 25 ml of tetrahydrofuran and 3 drops of carbon tetrachloride and the whole is heated at the boil under reflux for 30 minutes. The remainder of the 2-nonylbromobenzene solution is then added dropwise over a period of one hour and the reaction mixture is maintained under reflux for 2 hours. After dilution with 40 ml of tetrahydrofuran the whole is cooled in an ice bath to approximately 5° and a solution of 11.6 ml of dimethylformamide in 20 ml of tetrahydrofuran is added dropwise over a period of 15 minutes. After stirrin9 for one hour at room temperature, 250 ml of saturated ammonium chloride solution are added to the reaction mixture, the organic layer is separated off and the aqueous layer is extracted three times with ether. The residue that remains after the combined ethereal extracts have been dried and concentrated by evaporation is purified by chromatography on silica gel with mixtures of petroleum ether with an increasing amount of methylene chloride, yielding the desired 2-nonylbenzaldehyde in the form of a pale yellow liquid.
IR ($CH_2Cl_2$): 2920, 2850, 1695, 1600 cm$^{-1}$.

(b) Nonylbenzyl alcohol 0.57 g of sodium borohydride is added in portions, over a period of 15 minutes, to a stirred solution of 9.3 g of 2-nonylbenzaldehyde in 150 ml of methanol. After stirring for a further 30 minutes, the reaction mixture is concentrated by evaporation under reduced pressure and the residue is taken up in ether. The organic phase is washed with ice-cooled 0.2N hydrochloric acid and with water, dried over sodium sulphate and concentrated by evaporation in vacuo. Chromatographic purification of the residue on silica gel with mixtures of petroleum ether with an increasing amount of ether yields 2-nonylbenzyl alcohol in the form of a pale yellow oil.
IR ($CH_2Cl_2$): 3600, 2925, 2855, 1000 cm$^{-1}$.

(c) 2-nonylbenzyl bromide

A solution of 10 g of phosphorus tribromide in 50 ml of benzene is added dropwise over a period of 15 minutes to a stirred mixture of 6.6 g of 2-nonylbenzyl alcohol and 50 ml of benzene. The reaction mixture is heated under reflux for 30 minutes and, after cooling, ice-water and ether are added. The organic phase is separated off, washed with water, dried over sodium sulphate and concentrated by evaporation in vacuo. Chromatographic purification of the residue on silica gel with petroleum ether yields 2-nonylbenzyl bromide in the form of a colourless oil.
IR ($CHd_2Cl_2$): 2920, 2850, 1470, 1210 cm$^{-1}$.

(d) 2-nonylbenzyl-triphenylphosphonium bromide

A mixture of 7.2 g of 2-nonylbenzyl bromide, 5.77 g of triphenylphosphine and 60 ml of toluene is heated under reflux for 4 hours, cooled and diluted with 80 ml of ether. The 2-nonylbenzyl-triphenylphosphonium bromide that separates out is removed by filtration, washed with ether and dried in vacuo; m.p. 174°–176°.

(e) 3(RS),4(RS)-3,4-epoxy-1-(2-nonylphenyl)-1-trans-octene 6.4 ml of a 1.6M solution of butyllithium in hexane are added to a mixture, cooled to 5° and stirred under an argon atmosphere, of 5.6 g of 2-nonylbenzyl-triphenylphosphonium bromide and 50 ml of absolute tetrahydrofuran. After a further 10 minutes a solution of 2(RS),3(RS)-2,3-epoxyheptanal in 15 ml o tetrahydrofuran is added dropwise within a period of 3 minutes. The mixture is stirred for a further one hour at 5° and for 15 minutes at room temperature, water is added and extraction is carried out three times with ether. The organic phase is dried over sodium sulphate and concentrated. The residue remaining is suspended in hexane and filtered, and the filtrate is concentrated by evaporation under reduced pressure. Chromatographic purification of the residue on silica gel and elution with a 97:3 mixture (v/v) of petroleum ether/ether yields 3(RS),4(RS)-3,4-epoxy-1-(2-nonylphenyl)1-trans-octene;
IR ($CH_2Cl_2$): 2960, 2930, 2860, 1470, 870 cm$^{-1}$.

EXAMPLE 15:

3-[3(RS),4(SR)-4-hydroxy-1-(2-nonylphenyl)-1-trans-octen-3-ylthio]-propionic acid The methyl ester of the title compound is reacted analogously to Example 6. The title compound is obtained in the form of a solid, m.p. 28°–30° C. IR (CH$_2$Cl$_2$): 3590, 3000, 2960, 2930, 2860, 1750, 1710, 1470 cm$^{-1}$.

EXAMPLE 16:

N-[S-3(S),4(R)-4-hydroxy-1-(4-octylphenyl)-octenyl-N-trifluoroacetylcysteinyl]-glycine methyl ester (mixture of cis-/trans-isomers 60:40)

The title compound (cis-/trans-isomeric mixture 60:40) is obtained in a manner analogous to that described in Example 3 but starting from 3(R),4(R)-3,4-epoxy-1-(4-octylphenyl)-1-octene (mixture of cis-/trans-isomers 60:40) and N-(N-trifluoroacetylcysteinyl)-glycine methyl ester.

The 3(R),4(R)-3,4-epoxy-1-(4-octylphenyl)-1 -octene (mixture of cis-/trans-isomers 60:40) used as starting material can be obtained in the following manner:

(a) 2-trans-heptenol 16.9 g of 2-heptinol in 200 ml of ether are added dropwise within a period of 30 minutes, at 0° C., while stirring, to a solution of 10 g of lithiumaluminium hydride in 400 ml of ether and the resulting reaction mixture is boiled under reflux overnight. The excess of LiAlH$_4$ is destroyed by the addition of 40 ml of ethyl acetate while cooling in an ice-water bath and the resulting reaction mixture is taken up between ether and cold 1N sulphuric acid. The acidified (pH 2) aqueous layer is then again extracted with ether and the combined organic extracts are dried over magnesium sulphate and concentrated by evaporation in vacuo. Distillation of the residue (18 g) under reduced pressure yields 13.2 g of 2-trans-heptenol in the form of a colourless oil; m.p. 71°–72° C./13 mbar.

(b) 2(R),3(R)-2,3-epoxyheptanol 25.7 g of 2-trans-heptenol (see above) and 40 ml of a 3.2M solution of tert.-butyl hydroperoxide in toluene are added in succession, at −23° C. under anhydrous conditions, to a stirred solution of 66.3 ml of tetraisopropyl orthotitanate and 38.51 ml of D-(−)-tartaric acid diethyl ester in 1.1 liters of methylene chloride, the whole is maintained at −20° C. for 16 hours and, at −23° C., treated dropwise with 56 ml of 10% strength aqueous L-tartaric acid solution. After a further 30 minutes, the mixture is allowed to warm up to +20° C. and further stirred until the organic layer can clearly be separated off. This is stirred for 1 hour with 1 litre of 1% strength aqueous sodium sulphite solution, separated off, washed with water, dried over sodium sulphate and concentrated in a water-jet vacuum. The residue is dissolved in 1.6 liters of diethyl ether and cooled to 0° C.; 675 ml of N sodium hydroxide solution are added dropwise and the whole is stirred for 30 minutes at 0° C. The separated organic phase is washed with saturated sodium chloride solution, dried and concentrated, yielding 2(R),3(R)-2,3-epoxyheptanol in the form of a colourless unstable liquid, which is immediately processed in the next stage.

(c) 2(S),3(R)-2,3-epoxyheptanal

A solution of 13.3 g of 2(R),3(R)-2,3-epoxyheptanol in 100 ml of methylene chloride is added dropwise within a period of 30 minutes to a stirred suspension of 110.1 g of pyridinium chlorochromate and 41.9 g of sodium acetate in 500 ml of methylene chloride, the temperature being maintained at 25° C. by cooling gently. After 3 hours, the reaction mixture is diluted with 500 ml of diethyl ether and filtered over silica gel. The filtrate is washed with phosphate buffer of pH 8, dried over sodium sulphate and concentrated by evaporation. Chromatography of the residue on silica gel with a mixture of petroleum ether (b.p. 30°–45°) and diethyl ether (3:2) yields 2(S),3(R)-2,3-epoxyheptanal in the form of a colourless liquid.

(d) 4-ootylbenzaldehyde 68.3 g of titanium tetrachloride are added to a solution, cooled to −25° C., of 45.7 g of octylbenzene in 100 ml of chloroform under argon. 27.6 g of dichloromethyl methyl ether are then added dropwise at −25° C. within a period of 30 minutes and the whole is stirred for a further 1.5 hours at this temperature. The reaction mixture is poured onto ice-water, and the organic phase is separated off and washed neutral with water. After drying over magnesium sulphate and concentration by evaporation in vacuo, the residue is purified by chromatography on silica gel with hexane/ethyl acetate=(19:1). First of all a small amount of 2-octylbenzaldehyde is eluted, then the title compound (colourless oil).

IR (CH$_2$Cl$_2$): 2940, 2870, 1700, 1615, 1220, 1175 cm$^{-1}$.

(e) 4-octylbenzyl alcohol

Reaction of 4-octylbenzaldehyde analogously to Example 14b yields the title compound in the form of a colourless liquid.

IR (CH$_2$Cl$_2$): 3620, 2950, 2875, 1465, 1010 cm$^{-1}$.

(f) 4-octylbenzyl bromide 4-octylbenzyl alcohol is reacted analogously to Example 14c. The title compound is obtained in the form of a colourless solid.

IR (CH$_2$Cl$_2$): 2940, 2870, 1520, 1475, 1235, 1210 cm$^{-1}$.

(g) 4-octylbenzyl-triphenylphosphonium bromide

Reaction of 4-octylbenzyl bromide analogously to Example 14c yields the title compound in the form of a solid; m.p. 160°–161° C.

(h) 3(R),4(R)-3,4-epoxy-1-(4-octylphenyl)-1-octene (mixture of cis-/trans-isomers 60:40)

In a manner analogous to that described in Example 9a, but starting from 4-octylbenzyl-triphenylphosphonium bromide and 2(S),3(R)-2,3-epoxyheptanal, the title compound (cis-/trans-isomeric mixture 60:40) is obtained in the form of a light-yellow oil.

EXAMPLE 17:

Sodium salt of N-[S-3(S),4(R)-4-hydroxy-1-(4-octylphenyl)-1-octenyl-N-trifluoroacetylcysteinyl]-glycine (mixture of cis-/trans-isomers 60:40)

The cis-/trans-isomeric mixture (60:40) of the corresponding methyl ester is reacted analogously to Example 2. The title compound is obtained in the form of a cis-/trans-isomeric mixture (60:40); m.p. 120°–121° C.

EXAMPLE 18:

3-[1(RS),2(SR)-6-fluoro-2-hydroxy-1-(2-nonylphenyl)-hexylthio]-propionic acid methyl ester The title compound is obtained in the form of a pale yellow oil in a manner analogous to that described in Example 4 by using 1(RS),2(RS)-1,2-epoxy-6-fluoro-1-(2-nonylphenyl)-hexane instead of 1(RS),2(RS)-1,2-epoxy-1-(2-dodecylphenyl)-pentane.

IR ($CH_2Cl_2$): 3580, 2930, 2860, 1735, 1440, 1245 $cm^{-1}$.

The 1(RS),2(RS)-1,2-epoxy-6-fluoro-1-(2-nonylphenyl)-hexane used as starting material can be manufacture for example, as follows:

(a) 1-(2-nonylphenyl)-1-trans-hexen-6-ol 2.8 g of lithiumaluminium hydride are added in portions, over a period of approximately one hour, to a solution, stirred under a nitrogen atmosphere, of 34.4 g of 6-(2-nonylphenyl)-5-hexenoic acid methyl ester (cf. EP-OL 0 123 543) in 300 ml of absolute tetrahydrofuran. After a further 10 minutes 30 ml of ethyl acetate and then 30 ml of water are added dropwise. The reaction mixture is acidified by the addition of 1N hydrochloric acid and extracted repeatedly with ethyl acetate. After the combined organic phases have been dried and concentrated by evaporation, the crude product that remains is purified by chromatography on silica gel with dichloromethane to yield the title compound in the form of a yellowish oil.

IR ($CH_2Cl_2$): 3620, 2930, 2850, 1470, 970 $cm^1$.

(b) 6-fluoro-1-(2-nonylphenyl)-1-trans-hexene

A solution of 8.17 g of -(2-nonylphenyl)-1-trans-hexen-6-ol in 20 ml of dichloromethane is added dropwise over a period of 20 minutes to a mixture, cooled with an ice-bath and stirred under an argon atmosphere, of 4.68 g of diethylaminosulphur trifluoride in 20 ml of dichloromethane. After further stirring at room temperature for 14 hours, water is added, and the organic layer is separated off and washed with saturated sodium bicarbonate solution and water. The crude product remaining after the organic phase has been dried and concentrated by evaporation is purified by flash chromatography on silica gel with petroleum ether. The title compound is obtained in the form of a colourless oil.

IR ($CH_2Cl_2$): 2930, 2850, 1465, 970 $cm^{-1}$.

(c) 1(RS),2(RS)-1,2-epoxy-6-fluoro-1-(2-nonylphenyl)hexane

The title compound is obtained in the form of a colourless oil in a manner analogous to that described in Example 3c by using 6-fluoro-1-(2-nonylphenyl)-1-trans-hexene instead of 1-(2-nonylphenyl)-1-trans-hexene.

IR ($CH_2Cl_2$); 2920, 2850, 1455 $cm^{-1}$.

EXAMPLE 19:

Sodium salt of 3-[1(RS),2(SR)-6-fluoro-2-hydroxy-1-(2-nonylphenyl)-hexylthio]propionic acid A mixture of 1.7 g of 3-[(RS),2(SR)-6-fluoro- 2-hydroxy-1-(2-nonylphenyl)-hexylthio]-propionic acid methyl ester, 5 ml of tetrahydrofuran, 10 ml of methanol and 2.09 ml of 2N sodium hydroxide solution is stirred under argon for 14 hours at room temperature and for 2 hours at 45° C. Subsequently, the whole is concentrated by evaporation in vacuo at 45° C. and the residue is partitioned between dichloromethane and 1N hydrochloric acid. The residue remaining after the organic phase has been dried and concentrated by evaporation is purified on silica gel using dichloromethane with an increasing amount of methanol. The resulting acid is taken up in 10 ml of methanol/tetrahydrofuran (1:1), one equivalent of 1N sodium hydroxide solution is added and the whole is stirred for 10 minutes at room temperature. The residue remaining after the volatile components have been removed is evaporated twice with chloroform. The title compound is obtained in the form of a yellowish amorphous solid.

IR ($CH_2Cl_2$): 2930, 2860, 1600, 1430, 1400 $cm^{-1}$.

Examples of pharmaceutical compositions and corresponding medicaments in finished form.

There is to be understood hereinafter by the term "active ingredient" a compound of the formula I according to the invention, especially one that is described as a product in Examples 1–9, such as, for example, the sodium salt of 3-[S-4(RS),5(SR)-4-hydroxy-1,1,1-trifluoro-6-cis-icosen-5-ylthio]-propionic acid or the sodium salt of 3-[1(RS),2(SR)-2-hydroxy-1-(2-nonylphenyl)-hexylthio]propionic acid.

Example A:

An inhalation suspension forming a solid aerosol, containing propellant and 0.1 % by weight of active ingredient.

| Composition: | % by weight |
| --- | --- |
| active ingredient, micronised | 0.1 |
| sorbitan trioleate | 0.5 |
| propellant A (trichlorotrifluoroethane) | 4.4 |
| propellant B | |
| (dichlorodifluoromethane and | 15.0 |
| 1,2-dichlorotetrafluoroethane) | 80.0 |

Manufacture: With the aid of a customary homogeniser, the active ingredient is suspended, with the exclusion of moisture, in trichlorotrifluoroethane with the addition of sorbitan trioleate, and the suspension is introduced into an aerosol container fitted with a dosing valve; the container is sealed and filled up under pressure with propellant B.

Example B:

An approximately 2% strength aqueous solution of an active ingredient in the form of its sodium or potassium salt, suitable for inhalation.

| Composition | |
| --- | --- |
| active ingredient (K or Na salt) | 2000 mg |
| disodium salt of ethylenediaminetetraacetic | 10 mg |

| Composition | |
|---|---|
| acid | |
| benzalkonium chloride | 10 mg |
| water, freshly distilled ad | 100 ml |

Manufacture: The active ingredient is dissolved in approximately 60 ml of freshly distilled water and the stabiliser (disodium salt of ethylenediaminetetraacetic acid) and preservative (benzalkonium chloride) are added. When all the components have completely dissolved, the resulting solution is made up to 100 ml and introduced into small pressurised bottles and these are sealed in gas-tight manner. The propellant is added as required, in the form of a gas under pressure or in liquid form.

APPENDIX-PHARMACOLOGICAL TEST METHODS

Bronchoconstriction test in guinea-pigs (in vivo, aerosol):

Male guinea pigs weighing from 400 to 700 g are anaesthetised intraperitoneally with 1.4 g/kg of urethane, and a polyethylene tube is introduced into the jugular vein. A second polyethylene tube is introduced into the trachea. The pressure in the oesophagus is measured by means of a tube which is introduced into the oesophagus and is connected to a Statham pressure transducer. The animal is placed in a Plexiglass chamber that can be sealed in an air-tight manner and that is connected to a Fleisch tube No. 000 and a Validyne transducer MP 45-1. The flow is measured by means of this arrangement.

After surgical preparation of the experimental animals, a certain time is allowed to elapse so that the pulmonary functions can stabilise. The compound to be tested is then administered in accordance with the following protocol. The experimental animals are exposed for one minute to a 1% aerosol solution of the compound to be tested (w/v) or to distilled water (for control purposes). For all test compounds that are administered by inhalation, a Monaghan ultrasound spray device (model 670) is used of which the particle size ranges from 1 to 8 microns, the majority being 3 microns.

Aqueous solutions are each freshly prepared and introduced by means of an on-stream drug vial into the chamber of the spray device. The spray mist produced is administered to the experimental animals via a 65 ml glass chamber which is connected to the trachea by a tube. At the end of the treatment period, $LTD_4$ (0.3 μg/ml) is administered for two minutes using a second Monaghan ultrasound spray device (model 670) and via an identical glass chamber.

The reduction in the compliance in the 3rd minute after $LTD_4$ administration is read by comparing the mean value of three animals with the mean value of three control animals and the percentage inhibition of the compliance is calculated in accordance with the following formula:

$$\% \text{ inhibition} = 100 - \frac{(100 - \text{compliance preparation}) \cdot 100}{(100 - \text{compliance control})}$$

If different concentrations of active ingredient are examined, the percentage inhibition for each concentration is recorded by entering the log concentration on the abscissa against the percentage inhibition on the ordinate. The $IC_{50}$ is then ascertained by linear regression analysis.

In vitro test for determining the inhibition of phospholipase $A_2$ obtained from human leucocytes Human neutrophilic polymorphonuclear leucocytes are isolated from "buffy coats" by multistage fractional sedimentation and are deep-frozen. Phospholipase $A_2$ is extracted from the cell suspension by homogenisation with the addition of ice-cold 0.36N $H_2SO_4$ in 2N NaCl, and the supernatant obtained after centrifugation at $10,000 \times g$ is dialysed against sodium acetate buffer pH 4.5.

In order to determine the enzyme activity, enzyme (10–30 μg protein) is incubated at 37° for 1 hour in 0.1M tris/HCl buffer pH 7 with the addition of 1 mM $CaCl_2$ and substrate consisting of phospholipids (2 μM) of *Escherichia coli* that have been radioactively labelled with $^{14}C$-oleic acid by means of biosynthesis. The reaction is stopped by the addition of Dole reagent (isopropanol/heptane/1N $H_2SO_4$ 40:10:1, v/v) and the $^{14}C$-oleic acid selectively released by phospholipase $A_2$ is extracted. Substrate also extracted at the same time is completely removed by filtering the extract through a column of silica gel. The $^{14}C$-oleic acid in the eluate is determined by radiometry.

In order to ascertain the inhibitory action of test substances on phospholipase $A_2$, these substances are added in the form of solutions in water, dimethyl sulphoxide (final concentration in the mixture up to 5% v/v) or ethanol (final concentration in the mixture up to 2.5% v/v) to the incubation mixture. The strength of action of the test substances is expressed by the $IC_{50}$, that is to say the concentration that causes a 50% inhibition of the control activity. The $IC_{50}$ is ascertained on a graph by plotting the percentage inhibition on the ordinate against the log of the concentration (μM) on the abscissa.

Under the test conditions described, mepacrine inhibits phospholipase $A_2$ with an $IC_{50}$ of 1600 μM.

In vitro test for determining the inhibition of phospholipase C obtained from human thrombocytes Human thrombocytes are obtained from "buffy coats" by fractional centrifugation and then deep frozen. The phospholipase C is released by ultrasound treatment of the cell suspension and, after ultracentrifugation ($150,000 \times g$ for 1 hour), is found in soluble form in the supernatant.

To ascertain the enzyme activity, enzyme (20–100 μg protein) is incubated at 37° for 5 minutes in 0.025M tris/malate buffer pH 6 with the addition of 0.2 mM $CaCl_2$ and 0.02 mM radioactively labelled substrate, phosphatidyl-[$^{14}C$]-inositol. The reaction is stopped by extraction by shaking with $CHCl_3/CH_3OH$ 2:1 (v/v). In the course of this operation unconsumed substrate is extracted into the organic phase, whilst the reaction product, $^{14}C$-inositol phosphate, remains in the aqueous phase and can be measured by radiometry of an aliquot.

In order to ascertain the inhibitory action of test substances on phospholipase C, these substances are added in the form of solutions in water, dimethyl sulphoxide (final concentration in the mixture up to 5%, v/v) or ethanol (final concentration in the mixture up to 2.5%, v/v) to the incubation mixture. The strength of action of the test substances is expressed by the $IC_{50}$, that is to say the concentration that causes a 50% inhibition of the control activity. The IC$_{50}$ is ascertained on a graph by plotting the percentage inhibition on the ordinate against the log of the concentration (μM) on the abscissa.

Under the test conditions described, mepacrine inhibits phospholipase C with an IC$_{50}$ of 20 μM.

We claim:

1. A compound of the formula

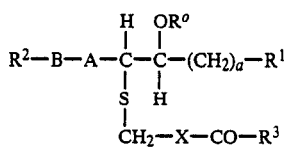  (I)

in which the general symbols have the following meanings:

a is an integer of from 1 to 7, $R^o$ represents hydrogen or $C_{1-7}$-alkanoyl, $R^1$ represents $C_{1-3}$-alkyl which may be substituted at the terminal carbon atom by hydroxy, by benzoyloxy, by $C_{1-7}$-alkanoyloxy, by a halogen atom having an atomic number of at most 17, or by methoxy, or represents $C_{1-3}$-perfluoroalkyl, $R^2$ represents an aliphatic radical having from 5 to 15 carbon atoms, A represents ethylene or alternatively, if $R^1$ represents a halogenated radical and/or B represents phenylene, then A is a single bond or vinylene, B represents a single bond or phenylene, $R^3$ represents hydroxy, $C_{1-7}$-alkoxy or an amino group or substituted amino group of the formula

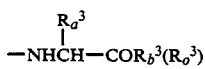

wherein $R_a^3$ is hydrogen or $C_{1-4}$-alkyl, and $R_b^3$ is hydroxy, $C_{1-7}$-alkoxy, or amino, —X— represents a single bond, a methylene group or a group of the formula $R_4$-NH-CH-(—Xo—) wherein $R_4$ is hydrogen or the acyl radical of (a) γ-glutamyl or (b) an alkanoic acid having a maximum of 7 carbon atoms, or $R_4$ is trifluoroacetyl, and salts of such compounds having salt-forming properties.

2. A compound according to claim 1 in which in formula I the O-atom of the hydroxy group is in the trans-configuration relative to the S-atom.

3. A compound according to claim 1 in which, in formula I $R^1$ represents trifluoromethyl and a=1 or 2.

4. A compound according to claim 1 in which in formula I $R^o$ represents hydrogen.

5. A compound according to claim 1 in which in formula I $R^2$-B-A together represent o- or p-($C_{5-15}$-alkyl) phenyl.

6. A compound according to claim 5 in which in formula I $R^2$ represents a linear alkyl having from 8 to 12 C-atoms.

7. A compound according to claim 1 in which in formula I $R^o$ represents hydrogen, $R^1$ represents trifluoromethyl, $R^2$-B-A together represent a linear 1-alkenyl having from 10 to 16 C-atoms and a represents an integer of from 1 or 2.

8. A compound according to claim 1 in which in formula I $R^3$ represents hydroxy or $C_{1-7}$-alkoxy.

9. A compound according to claim 1 in which $R^3$ represents a group of formula $R_o^3$ wherein $R_a^3$ is hydrogen and $R_b^3$ is hydrogen or $C_1$-$C_4$-alkoxy.

10. A compound according to claim 1 in which in formula I —X— represents a group of said formula —$X_o$—.

11. A compound according to claim 1 in which in formula I —X— represents a single bond or a methylene group.

12. A compound according to claim 1 in which in formula I a=1 or 2, $R^o$ represents hydrogen, $R^1$ represents trifluoromethyl, $R^2$-B-A together represent a linear $C_{10-16}$-1-alkenyl, $R^3$ represents hydroxy, $C_{1-7}$-alkoxy or a radical of the partial formula —NH—CH$_2$—COR (in which R represents hydroxy or $C_{1-7}$-alkoxy), and —X— represents a methylene group or a group of formula —$X_o$— in which $R^4$ represents hydrogen, acetyl or trifluoroacetyl, and salts of compounds having salt-forming properties.

13. A compound according to claim 12 in which in formula I a, $R^o$, $R^1$, A, B and $R^2$ have the meanings given therein and the grouping —S—CH$_2$—X—CO—R$^3$ represents a radical, bonded by the S-atom, of 3-mercaptopropionic acid or of the methyl ester or an alkali metal salt thereof.

14. A compound according to claim 12 in which in formula I a, $R^o$, $R^1$, A, B and $R^2$ have the meanings given therein and the grouping —S—CH$_2$—X—CO—R$^3$ represents a radical of the formula

in which $R_b^3$ represents hydroxy or $C_{1-4}$-alkoxy and $R^4$ represents hydrogen, acetyl or trifluoroacetyl, and alkali metal salts of compounds having salt-forming properties.

15. A compound according to claim 1 in which in formula I a=1 or 2, $R^o$ represents hydrogen, $R^1$ represents methyl, chloromethyl or fluoromethyl, A is a single bond, B represents phenylene, $R^2$ represents a linear $C_{5-15}$-alkyl, $R^3$ represents hydroxy or a radical of the partial formula —NH—CH$_2$—COOH and —X— represents a methylene group or a group of formula —$X_o$— which $R^4$ represents hydrogen, acetyl or trifluoroacetyl, and its salts.

16. A compound according to claim 15 in which in formula I a, $R^o$, $R^1$, A, B and $R^2$ have the meanings given therein and the grouping —S—CH$_2$—X—CO—R$^3$ represents a radical, bonded by the S-atom, of 3-mercaptopropionic acid or of an alkali metal salt thereof.

17. A compound according to claim 15 in which in formula I a, $R^o$, $R^1$, A, B and $R^2$ have the meanings given therein and the grouping —S—CH$_2$—X—CO—R$^3$ represents a radical of the formula

in which $R^4$ represents trifluoroaceyl, and its alkali metal salts.

18. N-{S-[4(RS),5(SR)-4-hydroxy-1,1,1-trifluoro-6-cis-icosen-5-yl]-N-trifluoroacetylcysteinyl}-glycine in the form of the methyl ester, free acid or an alkali metal salt, as compounds according to claim 1.

19. N-{S-[1(RS),2(SR)-4-hydroxy-1-(2-dodecylphenyl)pentyl]-N-trifluoroacetylcysteinyl}-glycine in the form of the methyl ester, free acid or an alkali metal salt, as compounds according to claim 1.

20. 3-[S-4(RS),5(SR)-4-hydroxy-1,1,1-trifluoro-6-cis-icosen-5-ylthio]-propionic acid in the form of the methyl ester, free acid or an alkali metal salt, as compounds according to claim 1.

21. 3-[1(RS),2(SR)-2-hydroxy-1-(2-nonylphenyl)-hexylthio]-propionic acid in the form of the methyl ester, free acid or an alkali metal salt, as compounds according to claim 1.

22. 3-[1(RS),2(SR)-2-hydroxy-1-(2-dodecylphenyl)-pentylthio]-propionic acid in the form of the methyl ester, free acid or an alkali metal salt, as compounds according to claim 1.

23. 3-[1(RS),2(RS)-2-hydroxy-1-(4-nonylphenyl)-hexylthio]-propionic acid in the form of the methyl ester, free acid or an alkali metal salt, as compounds according to claim 1.

24. A physiologically tolerable salt of one of the compounds according to claim 1 provided it has at least one free carboxy group.

25. A pharmaceutical composition comprising a therapeutically effective amount of for the alleviation or elimination of pathological conditions or symptoms that are attributable to the allergogenic action of leucotrienes or an inflammation, at least one compound according to claim 1 together with at least one pharmaceutically acceptable carrier.

26. The pharmaceutical composition according to claim 25 in a ready-to-use medicament form.

27. The pharmaceutical composition according to claim 25 suitable for administration by inhalation.

28. A therapeutic method for the alleviation or elmination of pathological conditions or symptoms in a mammal that are attributalbe to the allergogenic action of leucotrienes or an inflammation comprising administering to said mammal an effective dose of a compound according to claim 1.

29. The method according to claim 28 wherein said mammal is a human.

* * * * *